United States Patent [19]

Shinitzky et al.

[11] Patent Number: 4,931,275

[45] Date of Patent: Jun. 5, 1990

[54] ANTI-TUMOR VACCINES AND THEIR PREPARATION

[75] Inventors: Meir Shinitzky; Irun R. Cohen, both of Rehovot, Israel

[73] Assignee: Yeda Research & Development Co., Ltd., Rehovot, Israel

[21] Appl. No.: 198,691

[22] Filed: May 24, 1988

Related U.S. Application Data

[63] Continuation of Ser. No. 803,556, Dec. 2, 1985, abandoned.

[51] Int. Cl.$^5$ .......................... C07K 3/02; C07K 3/08; C07K 3/28; A61K 39/00

[52] U.S. Cl. ........................................ 424/88; 424/90; 424/89; 424/93; 514/2; 514/8; 514/21; 530/350; 530/395; 530/403; 530/427; 530/806; 530/828; 530/406; 435/240.1; 435/240.2

[58] Field of Search ............... 530/387, 395, 350, 351, 530/403, 406, 828; 424/93, 88, 90, 89; 514/2, 8, 21; 435/240.2, 240.1

[56] References Cited

U.S. PATENT DOCUMENTS

4,634,590 1/1987 Cohen et al. ......................... 424/88

OTHER PUBLICATIONS

Shinitzky et al, PNAS 76, 1979, pp. 5313-5316.
Shinitzky et al, CA #137302e, vol. 98, 1983.
Shinitzky et al, CA #21248k, vol. 100, 1984.
Hoeven et al, Biochimica et Biophysica Act, 1979, 551, pp. 44-54.
Richert et al, Cancer Immunol. Immunother., 22, pp. 119-124.
Peters et al, JNCI, 1980, 64(6), pp. 1521-1525 (abstract).
Shinizky et al—"Regulation of Tumour Growth by Lipids—Possible Clinical Applications", Dev. Cancer Res., 1982, 7 (Membr. Tumour Growth), 61-68.
Shinizky et al—"Regulation of Membrane Function by Lipids; Implications for Tumor Development", Prog. Clin. Biol. Res., 1983, 132B (Int. Cancer Congr. 13th, 1982, Part B), 425-433.
Borochov et al.—"Vertical Displacement of Membrane Proteins Mediated by Changes in Microviscosity", Proc. Natl. Acad. Sci. USA, vol. 73, No. 12, 4526-4530, 1976.
Skornick et al—"Positive Skin Tests with Autologous Tumor Cells of Increased Membrane Viscosity", Cancer Immunology and Immunotherapy, 11, 93-96, 1981.
Muller et al—"Passive Shedding of Erythrocyte Antigens Induced by Membrane Rigidification", Exp. Cell Research, 136:53-62, 1981.
Chong—"Pressure Effects on Liposomes, Biological Membranes and Membrane Bound Proteins", Diss. Abstr. Int. B, 43(9), 2876 (1983).
Zimmerman et al—"The Effects of Hydrostatic Pressure on Cell Membranes", Chemical Abstracts, 88:17431f (1978).
Macdonald—"Molecular and Cellular Effects of Hydrostatic Pressure; a Physiologist's View", Chemical Abstracts, 95:110223u (1981).
Clark et al—"X-ray Diffraction Studies at Globular Proteins, III. The Action of Formaldehyde on Proteins", Chemical Abstracts, 31:3071-2 (1937).
Jung et al—"Linkage of Formaldehyde to and its Effect on Erythrocytes", Chemical Abstracts, 49:6338f (1955).
Shinitzky et al—"Microviscosity Parameters and Protein Mobility in Biological Membranes", Chemical Abstracts, 84:160894g (1976).

Primary Examiner—Margaret Moskowitz
Assistant Examiner—Jeff Kushan
Attorney, Agent, or Firm—Browdy & Neimark

[57] ABSTRACT

There are provided anti-tumor vaccines which contain as active ingredient tumor cells which have been pressure treated so as to augment their antigenic properties, tumor cells treated with cholesteryl hemisuccinate (CHS) and subsequently pressure treated, or plasma membranes from either of, or membrane proteins shed from either of these cells, or a combination of any of these. According to another embodiment, tumor cells are treated with cholesteryl hemisuccinate or by the application and release of pressure, and subsequently with a cross-linking agent. Such cells, plasma membranes obtained from these and proteins shed from the surface of these are effective active ingredients in anti-tumor vaccines.

35 Claims, No Drawings

ANTI-TUMOR VACCINES AND THEIR PREPARATION

This application is a continuation of application Ser. No. 803,556, filed Dec. 2, 1985, now abandoned.

FIELD OF THE INVENTION

The invention relates to anti-tumor vaccines for use in human and veterinary medicine. The active ingredient of such vaccines are tumor cells the antigenicity of which has been increased by certain treatments, plasma membranes obtained from such treated cells, or proteins shed from the surface of such treated cells. The invention further relates to the production of such vaccines and to methods of treatments based on the use of such vaccines.

Experiments have demonstrated that EL-4 T-leukemia cells treated in vitro as set out above, plasma membranes obtained from such treated cells, or proteins shed form the surface of such cells or membranes can be used as active ingredient in vaccines which effectively immunize laboratory animals against the subsequent challenge by such tumor cells.

BACKGROUND OF THE INVENTION

Cancer vaccines made from autologous cell preparations are based on the well established fact that tumor cells bear specific neo-antigens. The immunogenicity of cancer cells is too weak to elicit a pronounced immune reaction capable of coping with tumor development in cancer patients. Also artificial coupling of such tumor cells with strong antigens failed to give adequate results.

Since 1976 the "vertical displacement" approach, Borochov et Shinitzky, Proc. Nat. Acad. Sci., U.S.A. 73, 4526–30 (1976) has been used to enhance the immunogenicity of tumor cells. Increase of membrane lipid microvisocosity results in an exposure of latent antigens which render the system more immunogenic. It has been shown that rigidification of the membrane by incorporation of cholesteryl hemisuccinate (CHS) enhances the exposure of the effective antigens and that such cells can be used with a greater degree of success for immunization of mice against certain tumors, Shinitzky et al., Proc. Natl. Acad. Sci. U.S.A. 76 5313–5316 (1979). This provides a potential anti-tumor vaccine.

The clinical potential of these findings was examined by delayed type hypersensitivity reaction (skin-test) in patients with solid tumors against their autologous irradiated tumor cells. Only upon enrichment with CHS a strong response could be detected, Skornick et al. Cancer Immunolo. Immunother. 11, 93–96 (1981).

The vertical displacement of proteins was used to shed off blood group antigens of human erythrocytes, Muller and Shinitzky, Exp. Cell Res. 136, 53–62 (1981). This illustrates that by the combination of CHS and hydrostatic pressure it is possible to isolate surface proteins without the use of detergents which are undesired as they tend to denature such proteins.

SUMMARY OF THE INVENTION

There are provided effective vaccines for use in human and veterinary medicine. The anti-tumor vaccines contain as active ingredient certain specific types of tumor cells which have been treated so as to augment their antigenicity, or plasma membranes obtained from such treated cells, or tumor antigens shed from the surface of such treated cells (proteins shed from such surfaces of treated cells). There is provided a process for augmenting the antigenicity of tumor cells by the application and release of relatively high pressures. There is further provided a process for chemically treating such cells (as for example by means of cholesteryl hemisuccinate and the subsequent pressure treatment); there is also provided a process for augmenting the antigenicity of such pressure treated or cholesteryl hemisuccinate treated cells, by means of a suitable cross-linking agent (formaldehyde or suitable bifunctional agent). There is further provided a process for isolating certain surface constituents from such treated cells: these may be plasma membranes or tumor antigen associated proteins. Any of these can be used as active ingredient in a suitable carrier to provide effective anti-tumor vaccines.

The methods of the present invention essentially maintain the biological activity of the cells or of their constituents used for such vaccines. The immunogenicity is essentially maintained and thus the resulting vaccines can be used for the immunization and also for the treatment of patients afflicted with certain types of tumor.

The cross-linking is advantageously effected by treating in vitro suitable tumor cells with a chemical cross-linking agent in a suitable medium, such as PBS buffer. Advantageous results were obtained by treating cells, or cells pretreated with cholesteryl hemisuccinate, in a buffer solution (PBS) containing about 2 per cent formaldehyde or 2 per cent glutaraldehyde for about 1 h at room temperature. Under such conditions chemical cross-linking results in a certain fixing of the antigenic display on the cell surface, augmenting the antigenicity of such surface layer. Cells thus treated, plasma membranes obtained from such cells, or proteins shed from such cells have advantageous antigenic properties when used in vaccine form.

It has been established that tumor cells of certain laboratory animals, and especially mice, when treated as set out above, have a substantially augmented antigenicity against such tumor cells. Such cells, and the plasma membranes and surface proteins shed from the surface of such cells (treated as set out above), are effective ingredients in vaccines. The invention is of special applicability to solid tumors. Experiments have shown that when administered prior to the challenge with viable tumor cells or shortly after the application of such cells, as those used for vaccine preparation, the incidence of tumors is greatly reduced, and survival after challenge is prolonged. The rate of tumor growth and of metastatic dissemination are reduced.

Preliminary experiments with tumor cells and of immunogens shed from human solid tumors treated with cross-linking agents demonstrate that they have an effectivity in anti-cancer vaccination and that they have an effectivity in allogeneic treatment according to the type and stage of the tumor.

There have been carried out tests with treated cells and with proteins shed from tumor cell plasma membranes either by a combination of CHS treatment and hydrostatic pressure or by hydrostatic pressure alone followed by cross-linking. Experimental tumors tested were the T-leukemia EL-4 in C57B1 mice and chemically induced carcinoma LSP-1 in hamsters.

The cells and immunogens shed from these two types of tumor cells were found to be immunogenic as evident by a substantial delay in tumor development when immunization with such proteins was given prior to tumor implantation.

Experiments were carried out with human patients with tumor cells treated with a cross-linking agent and with immunogens shed from their CHS-pressure or pressure alone treated tumor cells and with plasma membranes of these. Skin reaction tests were made with 9 patients who displayed only a weak reaction with CHS treated cells, and the results indicate that precipitated membrane fragments or protein aggregates or soluble membrane proteins have an immunogenic potential stronger than that of CHS treated cells. The results are summarized in Table 2.

DESCRIPTION OF THE PREFERRED EMBODIMENT

Either hydrostatic pressure alone or a combination of treatment of the cells with CHS and application of hydrostatic pressure were used to obtain cells with augmented antigenicity or membrane proteins or plasma membranes which were used as active ingredient in the vaccines of the invention.

Most of the proteins thus obtained stay in solution as soluble proteins, presumably through support of bound phospholipids which are shed off simultaneously. The shedding off seems to result from vertical or lateral displacement of the freely diffusible protein upon increase of the lipid microviscosity. In practice, this is brought about by pretreatment with CHS, to moderately rigidify the plasma membrane lipid layer, followed by hyperrigidification with hydrostatic pressure, followed by further treatment with a cross-linking agent.

The procedure used is outlined in the following. For CHS incorporation a sterile medium ("PVP medium") consisting of 3.5% polyvinyl pyrrolidone, PVP (40.000 MW), 1% bovine serum albumin and 0.5% glucose in phosphate buffered saline, PBS, is used. An ethanolic solution of 5 mg/ml CHS is diluted 1:50 or 1:100 into the PVP medium to form homogenous dispersion of 50 or 100 μg/ml CHS. Tumor cells are incubated in the PVP-CHS dispersion ($10^6$ cells per ml) at room temperature for up to 90 min. The incorporation of CHS, and therefore the increase in the plasma membrane microviscosity, is approximately linear with incubation time up to 90 min. Attention is given to the possibility of shedding of tumor immunogens into the medium during the longer incubation periods.

Pressure (French Press) is applied as previously described, Muller C. P. and Shinitzky M. Exp. Cell Res. 136, 53–62(1981). The CHS enriched cells or cells without any pretreatment are washed and dispersed in sterile PBS as a dense dispersion ($\sim 10^8$ cells per ml) in a capped Eppendorff plastic tube ($\sim 1.5$ ml) filled to the top. A short needle stuck through the cap serves as a vent for pressure equalization. Both the tube and the needle are filled with PBS without any air bubbles to avoid cell rupture. The tubes (up to 4) are then placed in a 40 ml pressure bomb (Aminco) filled with PBS and sealed. Pressure is applied gradually to reach after 15 min the maximum (up to 1500 atm.) and after 30–60 min it is slowly released ($\sim 15$ min). Under such conditions the viability of most cells is preserved ($\sim 80\%$), though the morphology of the cells can be markedly distorted, presumably due to loss of membrane material. The pressurized cells are centrifuged and both the supernatant and the cells are collected. The supernatant is then ultracentrifuged for 1 hr at 110.000 g to separate between shed membrane fragments or protein aggregates ("shed fragments") which constitute the precipitate and soluble monomeric or oligomeric proteins ("shed soluble proteins") which remain in the supernatant. When required, further fractionation of the shed soluble proteins is carried out by gel filtration. The pressure treated cells and plasma membranes of these are also effective in vaccines.

The above described method for producing tumor cells of increased antigenicity and for isolation of tumor immunogens (as well as other membrane proteins like receptors and enzymes) as well as plasma membranes has important advantages over the conventional methods for isolation of membrane proteins which are based on membrane disintegration with detergents. In the latter, the detergent has an adverse denaturation effect on the isolated proteins and its subsequent separation is difficult and not always complete. In the novel method the cells and the isolated proteins retain their natural structure and activity presumably because of the strong association with a small amount of membrane phospholipids which prevent their aggregation. The shed immunogens can be obtained in a relatively large quantity within only a short period of time (hours). The pressurized cells treated with cross-linking agents, with or without irradiation, contain activated antigens and can be used for vaccination. A further improved antigenicity is obtained by chemical cross-linking.

HUMAN STUDIES

Solid tumors, mostly gastric carcinoma, bowel carcinoma and malignant melanoma, are used. Tumor cells are isolated from the viable portion of the growth immediately after surgery by mechanical means only. Cells are treated with CHS and pressure as described above or by pressure alone. The immunogens are prepared at concentrations required for skin tests ($10^6$ cells, or the material shed from them, in 0.2 ml sterile PBS) or for treatment [(2–5) $10^7$ cell, or the material shed from them in 1 ml sterile PBS]. Decision on which immunogen to use and the timing of the skin test or treatment are made according to the availability of material and the clinical condition of the patient.

EXAMPLE

Immunization Against the T-Leukemia EL-4

EL-4 cells ($10^8$ in 1 ml phosphate buffered saline, PBS) were subjected to hydrostatic pressure of 1500 atmospheres for 90 min at room temperature. Cells were separated by centrifugation and the supernatant was divided to fractions of 0.1 ml each used as a unit vaccine per mouse. Pressure treated cells were chemically cross-linked with 2% glutaraldehyde. Groups of ten C57B1 mice were treated as follows:

Group I—each animal was injected twice (7 days apart) with irradiated $10^7$ EL-4 cells in 0.1 ml PBS. (Control).

Group II—each animal was injected twice (7 days apart) with a unit of soluble vaccine described above.

Group III—each animal was injected twice (7 days apart) with $10^7$ cells after pressurization at 1200 atm. for 15 minutes and irradiation.

Group IV—isolated plasma membranes after chemical cross-linking of $10^7$ EL-4, treatment: 1200 atm. for 15 min (2% glutaraldehyde).

Group V—cells as in Group IV chemically cross-linked and pressure of 1500 atm. for 90 minutes.

Group VI—control: each animal injected twice (7 days apart) with 0.1 ml of PBS.

Seven days after the second injection the treated mice were challenged with $10^5$ viable EL-4 cells injected intraperitoneally and survival time after this challenge was determined. The mean survival time of each group (of 10 animals) was determined and this is presented in Table 1.

TABLE 1

| | Vaccine | Survival time (days) after challenge |
|---|---|---|
| Group I | irradiated cells | 30 |
| Group II | soluble antigens | 45 |
| Group III | pressurized irradiated cells | 90 |
| Group IV | membranes from cross-linking agent treated cells | 90 |
| Group V | Surface proteins shed from Group IV cells | 70 |
| Group VI | Control | 21 |

These results clearly demonstrate the immunogenic capacity of the proteins shed from EL-4 cells by hydrostatic pressure, as well as that of the pressurized cells and of their isolated plasma membranes. Each experimental group consisted of 10 animals.

TABLE 2

SKIN REACTIONS 36 HOURS AFTER INTRADERMAL INJECTION OF AUTOLOGOUS TUMOR MATERIAL(*)

| Subject (sex, age) | Tumor | | Skin reaction(**) 1 | 2 | 3 | 4 | 5 | PPD test |
|---|---|---|---|---|---|---|---|---|
| 1. B. M. male, 73 | Metastatic malignant melanoma | induration erythema | ± ++ | ± + | ± + | — ++ | — + | ± |
| 2. A. E. female, 56 | Primary breast carcinoma | induration erythema | — + | ± + | — ± | — + | — — | + |
| 3. A. S. female, 62 | Metastatic breast carcinoma | induration erythema | — ± | + + | ± ± | + ++ | ± ++ | + |
| 4. A. G. male, 61 | Primary carcinoma of the sigma | induration erythema | | ± + | ± + | + ++ | ± ++ | + |
| 5. H. I. female, 30 | Local recurrence of breast carcinoma | induration erythema | | | ± ± | ++ +++ | +++ +++ | + |
| 6. L. B. male, 72 | Carcinoma of the stomach | induration erythema | + + | ± ± | + + | + + | + ++ | + |
| 7. R. A. female, 74 | Local recurrence of breast carcinoma | induration erythema | — ± | ± — | — ± | ++ ++ | + +++ | + |
| 8. G. Y. female, 62 | Primary colon carcinoma | induration erythema | ± ± | + + | — ± | ++ ++ | — + | + |
| 9. B. Y. male, 68 | Hairy cell leukemia | induration erythema | — — | — — | — — | — — | — — | — |

(*) patients with weak skin reaction to CHS treated cells.
(**)
1. $10^6$ untreated tumor cells in 0.2 ml phosphate buffered saline (PBS).
2. $10^6$ CHS enriched cells in 0.2 ml PBS.
3. $10^6$ CHS enriched cells in 0.2 ml PBS after application of hydrostatic pressure (900 atm. 15 min at 4°).
4. Material precipitated after 20 min centrifugation at 100.000 g of the supernatant from 3 (suspended in PBS).
5. The supernatant of 4.
+ = <2 cm erythema diameter, <0.5 cm induration;
++ = 2 cm diameter; 0.5–1 cm induration;
+++ = >2 cm diameter; >1 cm induration.

We claim:

1. An immunogenic preparation comprising tumor cells treated so as to augment the antigenicity thereof, wherein said treatment to augment the antigenicity of the cells comprises the steps of:
   applying hydrostatic pressure to tumor cells dispersed in a buffer for a sufficient time and pressure to cause proteins to be shed from the surface membranes of said cells;
   chemically cross-linking said pressure-treated cells and shed proteins by subjecting said pressure-treated cells and shed proteins to a chemical cross-linking agent;
   fractionating said buffer containing said cross-linked pressure-treated cells and shed proteins, thereby forming a fraction containing said pressure-treated cross-linked cells and a supernatant fraction containing said cross-linked shed proteins; and
   isolating said pressure-treated cross-linked tumor cells.

2. An immunogenic preparation comprising plasma membranes of augmented antigenicity, wherein said plasma membranes are plasma membranes isolated from the pressure-treated cross-linked tumor cells or claim 1.

3. An immunogenic preparation in accordance with claim 1, wherein said cross-linked shed proteins comprise the shed membrane fragments or protein aggregates which are insoluble in said supernatant fraction obtained in said fractionating step.

4. An immunogenic preparation in accordance with claim 1, wherein said cross-linked shed proteins comprise the soluble monomeric or oligomeric proteins which are dissolved in said supernatant fraction obtained in said fractionating step.

5. An immunogenic preparation in accordance with claim 1, wherein said tumor cells used in said step of applying hydrostatic pressure are tumor cells which have previously been treated with cholesteryl hemisuccinate.

6. An immunogenic preparation in accordance with claim 1, wherein said tumor cells used in said step of applying hydrostatic pressure are tumor cells which have previously been treated with cholesteryl hemisuccinate.

7. An immunogenic preparation comprising plasma membranes of augmented antigenicity, wherein said plasma membranes are plasma membranes isolated from the pressure-treated cross-linked tumor cells of claim 5.

8. An immunogenic preparation in accordance with claim 1, wherein said tumor cells used in said step of applying hydrostatic pressure are autologous cells.

9. An immunogenic preparation in accordance with claim 1, wherein said tumor cells used in said step of applying hydrostatic pressure are solid tumor cells.

10. An immunogenic preparation in accordance with claim 1, wherein said tumor cells used in said step of applying hydrostatic pressure are leukemia, carcinoma, or melanoma cells.

11. An immunogenic preparation in accordance with claim 1, wherein said tumor cells used in said step of applying hydrostatic pressure are T-leukemia, breast carcinoma, stomach carcinoma or colon carcinoma cells.

12. A process of producing an immunogenic preparation containing tumor cells treated so as to augment the antigenicity thereof, comprising the steps of:
 applying hydrostatic pressure to tumor cells dispersed in a buffer for a sufficient time and pressure to cause proteins to be shed from the surface membranes of said cells;
 chemically cross-linking said pressure-treated cells and shed proteins by subjecting said pressure-treated cells and shed proteins to a chemical cross-linking agent;
 fractionating said buffer containing said cross-linked pressure-treated cells, thereby forming a fraction containing said pressure-treated cross-linked cells and a supernatant fraction containing said cross-linked shed proteins; and
 isolating said pressure-treated cross-linked tumor cells.

13. A process in accordance with claim 12, further including, prior to said applying step, the step of treating said tumor cells with cholesteryl hemisuccinate.

14. A process in accordance with claim 12, wherein said cross-linking is performed with formaldehyde or glutaraldehyde.

15. A process in accordance with claim 13, wherein said cross-linking is performed with formaldehyde or glutaraldehyde.

16. A process in accordance with claim 12, wherein the supernatant fraction containing said cross-linked shed proteins obtained in said fractionating step is further fractionated and the fraction with the greatest antigenicity is selected, and said isolating step comprises isolating said cross-linked shed proteins from said fraction with the greatest antigenicity.

17. A process in accordance with claim 12, wherein, in said applying step, said hydrostatic pressure is applied in the range of about 900 to about 1500 atm. for a period of time of 5-90 minutes.

18. A process in accordance with claim 12, wherein said tumor cells used in said step of applying hydrostatic pressure are autologous cells.

19. A process in accordance with claim 12, wherein said tumor cells used in said step of applying hydrostatic pressure are solid tumor cells.

20. A process in accordance with claim 12, wherein said tumor cells used in said step of applying hydrostatic pressure are leukemia, carcinoma or melanoma cells.

21. A process in accordance with claim 12, wherein said tumor cells used in said step of applying hydrostatic pressure are T-leukemia, breast carcinoma, stomach carcinoma or colon carcinoma cells.

22. An immunogenic preparation comprising shed tumor cell surface proteins of augmented antigenicity, said surface proteins being produced by the process comprising:
 applying hydrostatic pressure to tumor cells dispersed in a buffer for a sufficient time and pressure to cause proteins to be shed from the surface membranes of said cells;
 chemically cross-linking said pressure-treated cells and shed proteins by subjecting said pressure-treated cells and shed proteins to a chemical cross-linking agent;
 fractionating said buffer containing said cross-linked pressure-treated cells and shed proteins, thereby forming a fraction containing said pressure-treated cross-linked cells and a supernatant fraction containing said cross-linked shed proteins; and
 isolating said cross-linked shed proteins.

23. An immunogenic preparation in accordance with claim 22, wherein said tumor cells used in said step of applying hydrostatic pressure are autologous cells.

24. An immunogenic preparation in accordance with claim 22, wherein said tumor cells used in said step of applying hydrostatic pressure are solid tumor cells.

25. An immunogenic preparation in accordance with claim 22, wherein said tumor cells used in said step of applying hydrostatic pressure are leukemia, carcinoma, or melanoma cells.

26. An immunogenic preparation in accordance with claim 22, wherein said tumor cells used in said step of applying hydrostatic pressure are T-leukemia, breast carcinoma, stomach carcinoma or colon carcinoma cells.

27. A process of producing an immunogenic preparation containing surface proteins shed from tumor cells treated so as to augment the antigenicity thereof, comprising the steps of:
 applying hydrostatic pressure to tumor cells dispersed in a buffer for a sufficient time and pressure to cause proteins to be shed from the surface membranes of said cells;
 chemically cross-linking said pressure-treated cells and shed proteins by subjecting said pressure-treated cells and shed proteins to a chemical cross-linking agent;
 fractionating said buffer containing said cross-linked pressure-treated cells and shed proteins, thereby forming a fraction containing said pressure-treated cross-linked cells and a supernatant fraction containing said cross-linked shed proteins; and
 isolating said cross-linked shed proteins.

28. A process in accordance with claim 27, further including, prior to said applying step, the step of treating said tumor cells with cholesteryl hemisuccinate.

29. A process in accordance with claim 27, wherein said cross-linking is performed with formaldehyde or glutaraldehyde.

30. A process in accordance with claim 28, wherein said cross-linking is performed with formaldehyde or glutaraldehyde.

31. A process in accordance with claim 27, wherein, in said applying step, said hydrostatic pressure is applied in the range of about 900 to about 1500 atm. for a period of time of 5-90 minutes.

32. A process in accordance with claim 27, wherein said tumor cells used in said step of applying hydrostatic pressure are autologous cells.

33. A process in accordance with claim 27, wherein said tumor cells used in said step of applying hydrostatic pressure are solid tumor cells.

34. A process in accordance with claim 27, wherein said tumor cells used in said step of applying hydrostatic pressure are leukemia, carcinoma or melanoma cells.

35. A process in accordance with claim 27, wherein said tumor cells are used in said step of applying hydrostatic pressure T-leukemia, breast carcinoma, stomach carcinoma or colon carcinoma cells.

* * * * *